United States Patent [19]

Verma et al.

[11] 3,960,494
[45] June 1, 1976

[54] COLORIMETRIC ODORANT LEVEL TEST IN NATURAL, SYNTHETIC AND L.P. GAS AND THE LIKE

[75] Inventors: Arun Verma, Regina; Arthur R. Knight, Saskatoon, both of Canada

[73] Assignee: Saskatchewan Power Corporation, Regina, Canada

[22] Filed: Nov. 11, 1974

[21] Appl. No.: 522,331

[52] U.S. Cl. .............................. 23/232 R; 23/254 R; 23/259; 261/DIG. 65; 261/121 R; 206/222
[51] Int. Cl.² ................. B65D 25/08; G01N 31/22; G01N 33/22
[58] Field of Search .......................... 206/216, 222; 261/DIG. 65, 18 R, 121 R; 128/193, 194, 186, 214 C; 23/232 R, 254 R, 255 R, 259

[56] References Cited
UNITED STATES PATENTS

| | | | |
|---|---|---|---|
| 3,114,609 | 12/1963 | Jones | 23/232 R X |
| 3,208,828 | 9/1965 | Peurifoy et al. | 23/254 R X |
| 3,540,852 | 11/1970 | Gorne et al. | 23/254 R X |
| 3,713,780 | 1/1973 | Shapiro | 23/259 |
| 3,783,177 | 1/1974 | Kelso | 206/219 X |

Primary Examiner—Robert M. Reese
Attorney, Agent, or Firm—Stanley G. Ade

[57] ABSTRACT

Measuring of mercaptan-based odorants present in natural, synthetic, L. P. gases and the like. Conventionally, an operator smells the gas or uses apparatus which gives uncertain results. Alternatively, expensive laboratory equipment can be used, but this is not available to a field operator. The present test includes simple apparatus which can be connected to a gasline and which includes a disposable reagent tube having a plurality of liquid chemical reagents therein separated by membranes. The gas flow is bled through the first solution and then the solutions are mixed so that a color develops which can be compared with a standard color slide or the like thus indicating the quantity of the odorant in parts per million present in the gas.

7 Claims, 5 Drawing Figures

COLORIMETRIC ODORANT LEVEL TEST IN NATURAL, SYNTHETIC AND L.P. GAS AND THE LIKE

BACKGROUND OF THE INVENTION

This invention relates to a quantitative test for the determination of mercaptan-based odorants in natural, synthetic, L.P. gases and the like.

Conventionally, mercaptan-based odorants are used in gas so that escaping gas can be recognized by members of the general public. These odorants are usually injected into the gas supply prior to the supply entering the distribution facilities of a town or the like and if too much odorant is present, then the slightest leak causes widespread odors thus resulting in unnecessary complaints or reports from the general public. It should be understood mercaptan-based odorants normally used are extremely penetrating in their effect and that it is necessary to maintain the levels within fairly strict limits.

At the present time, there are methods of attempting to assess the amount of mercaptan-based odorant present and the most common method is for the operator to smell the gas. This method is qualitative in nature and depends on the olfactory nerve. It therefore has large variations in readings, depending on the operator, and apart from this inherent error, the operator with a cold is not able to perform the test.

Odorant measuring tubes have been used and this method involves the injection of a known volume of gas by a pump into a tube filled with a reactant which is absorbed on a granular material. The length of the developed stain due to the reaction is a measure of the odorant level, but in actual tests inconsistencies have been observed in the length of the stain which varies with the number of pump strokes and the concentration of odorant. Difficulty has also been observed in measurement of the actual length of the stain as there is no definite demarcation line between the end of the stain and the unstained material.

Titration also gives good quantitative results, but a minimum time of 30 minutes is required to conduct a single test. Furthermore, the apparatus itself is elaborate and requires a relatively high degree of operator skill. It also requires gas pressure greater than those on normal domestic service as the gas has to pass through several fritted glass bubblers.

Laboratory apparatus such as a gas chromatograph can of course be used with good quantitative results, but the size and high cost of the apparatus prohibit its use as a field instrument.

SUMMARY OF THE INVENTION

The primary object of the present invention is to provide a relatively economical and accurate test for measuring the level of odorants in a gas supply so that the test is readily available in large numbers to any gas producing or gas distributing organizations.

This is accomplished by using a disposable reagent tube having a plurality of chemical reagents therein. The gas is bubbled through one of the reagents and then the reagents are mixed together to produce a color, the intensity and shade of which is dependent upon the quantity of mercaptan-based odorants present. By comparing the resultant color with a standard color slide or the like, a direct reading of the quantity of the mercaptan-based odorant is possible, preferably in parts per million.

Another object of the invention is to provide a device of the character herewithin described which constitutes a simply conducted field test requiring a minimum of operator skill. However, it can also be used for precise laboratory measurements if desired.

Another object of the invention is to provide a device and method of the character herewithin described which requires a relatively short time to run and is not dependent on the olfactory nerve of the operator.

Still another object of the invention is to provide a device or method of the character herewithin described which utilizes disposable reagent tubes which are extremely economical.

A still further object of the invention is to provide a device and method of the character herewithin described which is simple in construction, economical in manufacture and otherwise well suited to the purpose for which it is designed.

With the foregoing objects in view, and other such objects and advantages as will become apparent to those skilled in the art to which this invention relates as this specification proceeds, our invention consists essentially in the arrangement and construction of parts all as hereinafter more particularly described, reference being had to the accompanying drawings in which:

BRIEF DESCRIPTION OF THE DRAWINGS

In the drawings like characters of reference indicate corresponding parts in the different figures.

DETAILED DESCRIPTION

Figure 1:
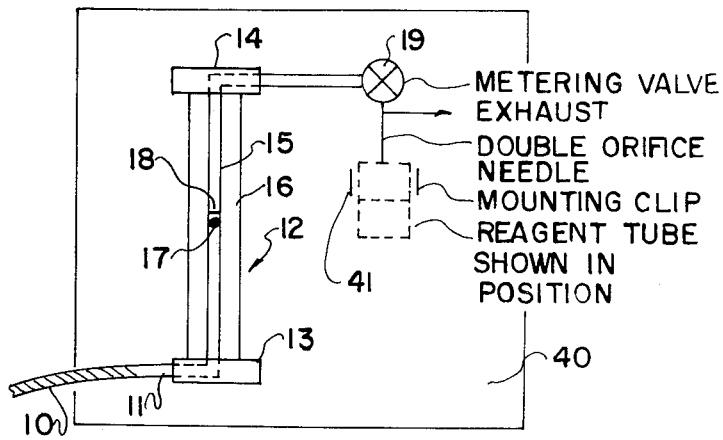
FIG. 1 is a front elevation in schematic form, of the flow injection apparatus.

Proceeding first to describe FIG. 1, a flexible tube or conduit 10 may be connected to a source of gas under pressure in order to ascertain the quantity of mercaptan-based odorant present in said gas. This is engaged over a connecting nipple 11 which communicates with a flow meter collectively designated 12. This includes a base 13 and an upper end 14 with a transparent vertical tube 15 extending between the base 13 and the upper end 14, supported by vertical member 16. A flow indicating ball 17 is situated within the tube 15 and a calibration mark 18 is provided on the tube so that when the ball is at the calibration mark, the required flow is present through the tube 15.

The upper end of tube 15 connects to a metering valve 19 which controls the flow of gas and this in turn leads to a means for injecting the gas into the reagent tube, said means being collectively designated 20.

In the present embodiment, the means 20 takes the form of a double orifice needle assembly having a main tubular portion 21 connected to the metering valve 19. An inner hollow membrane piercing portion 22 extends downwardly from the portion 21 and is connected with this portion as clearly shown in FIG. 4. A concentrically situated outer hollow exhaust portion 23 extends around the inner portion 22 and terminates spaced from the distal end of the inner portion as indicated by reference character 24 and a discharge portion 25 communicates with the annular space between the outer portion 23 and the inner portion 22 as clearly shown. The lower end of both portions 22 and 23 are adapted to pierce the membrane as will hereinafter be described. In both embodiments described below, the level of the reagent is spaced from the membrane so that the lower end of portion 23, when inserted through the membrane, is above the level of the liquid reagent to facilitate the exhausting of gas bubbled through the reagent.

Figure 4:
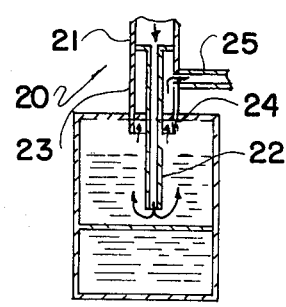
FIG. 4 is an enlarged sectional view showing one method of introducing the gas into one of the compartments of the reagent tube.

This means that gas may flow from the metering valve, through the portion 21 of the needle and through the inner portion 22 when it is situated within a reagent tube as illustrated in FIG. 4. Gas may then exhaust from the reagent tube, through the annular space between the inner and outer portions and thence through the discharge 25.

Figure 2:
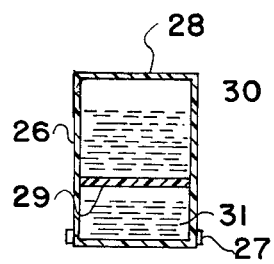
FIG. 2 is an enlarged vertical section of one of the reagent tubes.

Dealing first with the reagent tube illustrated in FIG. 2, it comprises a transparent cylindrical tube 26 having a bottom end closure 27 which is sealed onto the base of the tube. A frangible membrane 28 spans the upper end of the tube and is sealed to this upper end and a further membrane 29 spans the interior of the tube thus dividing the tube into two compartments 30 and 31.

Figure 5:
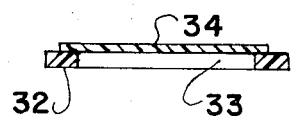
FIG. 5 is an enlarged cross sectional view showing one method of forming the intermediate membrane within the reagent tube.

FIG. 5 shows one method of forming the membrane which includes a disc 32 being centrally apertured as at 33 and having a frangible membrane 34 covering the aperture 33 and being secured to the surface of the disc by means of adhesive or the like.

However, there are many methods of forming the membrane and this does not constitute part of the present invention.

In the embodiment shown in FIG. 2, the reagent solutions are provided in both of the compartments 30 and 31, with air gaps between the solution and the membranes.

In the compartment 30 which is situated between membranes 28 and 29, the reagent comprises a solution of N-ethylmaleimide with alcohol being used as a solvent and the strength of this solution is between 0.0001 moles per liter up to a saturated solution.

The reagent solution in the compartment 31 which is situated between the membrane 29 and the base cap or cover 27, consists of a solution of alkali-hydroxide in alcohol having a strength of between 0.0001 moles per liter up to a saturated solution.

Figure 3:
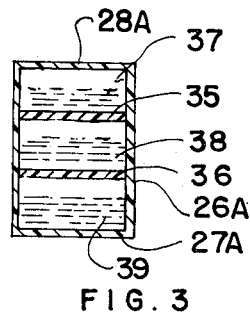
FIG. 3 is a view similar to FIG. 2, but showing a modified reagent tube.

FIG. 3 shows an alternative reagent tube which comprises a transparent tube 26A having a base cap 27A secured in a manner similar to that hereinbefore described.

An upper membrane 28A spans the upper end of the tube and in this embodiment, a pair of intermediate membranes are provided identified by reference characters 35 and 36. These divide the tube into three compartments. The first compartment 37 is situated between membrane 28A and membrane 35. The second compartment 38 is situated between membranes 35 and 36, and the third compartment 39 is situated between membrane 36 and the base cap or cover 27A.

The chemical reagent present in the first compartment 37 in this particular embodiment, is a solution of alkali-hydroxide in water having a strength of between 0.0001 moles per liter up to a saturated solution.

In one of the compartments 38 or 39, there is a solution of phosphomolybdic acid in water having a strength of between 0.0001 moles per liter up to a saturated solution and the other of these compartments, there is glacial acetic acid. It will be observed that the reagents in compartments 38 and 39 can be reversed in position. Once again air gaps are provided below the membranes and the surface of the reagent solutions.

The reagents described with reference to FIGS. 2 and 3 have the capability of producing a color if mercaptan-based odorants are present, when the reagents are mixed together and this principle is utilized in the determination of the property of the mercaptan-based odorants in any sample of gas.

The mercaptan in the odorant reacts with the N-ethylmaleimide (or phosphomolybdic acid) to form a pink (or blue in case of phosphomlybdic acid) colored soluble product that imparts its color to the solutions mixed in the tube.

Once the gas has been introduced into one of the reagents as will hereinafter be described, the reagents are mixed together and the resultant color is checked against a standard color slide or the like thus identifying with considerable accuracy, the amount of mercaptan-based odorants in parts per million present in the sample of gas.

Regardless of the embodiment of the tube used, it is clipped in position upon the mounting board 40 of the flow injection apparatus, being engaged between mounting clips 41 shown schematically in FIG. 1.

In either embodiment, the flexible tube 10 is connected to the nipple 11 and to the source of gas from a gas line or the like. The gas line valve (not illustrated) is opened and the flow metering valve 19 is adjusted until the flow indicating ball 17 reaches the calibration mark. The lines are purged and the reagent tube 26 or 26A is placed within the clips 41 and moved upwardly so that the needle assembly 20 pierces the upper membrane 28 or 28A only and is positioned as illustrated in FIG. 4, with the lower end of portion 22 immersed within the reagent solution and the lower end of the portion 23 being situated above the level of the liquid reagent in the air space or gap provided.

Gas is bubbled through the reagent in the uppermost compartment 30 or 37 for a predetermined time whereupon the flow meter valve 19 is closed. The reagent tube is then moved upwardly to break the membrane 29 in the case of the embodiment shown in FIG. 2 or to break both membranes 35 and 36 in the embodiment shown in FIG. 3, whereupon the reagent tube is removed from the needle assembly 20 and from the clips 41 and is shaken lightly to mix the solutions.

When the color is developed, it is compared with a standard color slide and this is read off in parts per million thus indicating the quantity of odorant present. Alternatively, the optical density may be measured at 5150 A with a colorimeter for the reagents used in the embodiment shown in FIG. 2 or at 8350 A for the reagents used in the embodiment shown in FIG. 3.

In either case, the reagent tubes should be kept in a container away from light until required for use and, after using, they are disposable.

It has been found that a gas flow of between 1 c.c. to 10 liters at a rate of between 1 c.c. and 10 liters per minute is satisfactory either through one or several needle assemblies 20 or similar gas dispersing tubes.

Thorough mixing of the solutions is of course required after the bubbling has taken place and a waiting period of between 0.5 and 60 minutes is necessary for pink color development for visual observation in the embodiment shown in FIG. 2 or for blue color development for visual observation in the embodiment shown in FIG. 3.

The maximum waiting period in both embodiments before quantitative measurement in the colorimeter is between 0.5 minutes to 4 hours.

The apparatus and method hereinbefore described gives an accurate economical and rapid method of ascertaining the quantity of mercaptan-based odorants present in a supply of gas and can be operated by relatively unskilled operators.

At the same time, the method and apparatus can also be used for precise laboratory method of measurement as the method is extremely accurate.

Since various modifcations can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. A method of measuring the quantity of mercaptan-based odorants in a gas stream comprising the steps of bubbling a sample of the gas through a first chemical reagent in a first compartment of a reagent carrying tube by piercing a membrane covering said first compartment, and then mixing the chemical reagent with at least one further chemical reagent in a second compartment of said tube and being separated from said first compartment by a further membrane spanning said tube, by piercing said second membrane, the mixing of said reagents producing a color in said mixture and then comparing the resulting color in said mixed reagents with a color shade standard.

2. The method according to claim 1 in which the chemical reagent in said first compartment comprises N-ethylmaleimide in alcohol having a strength of between 0.0001 moles per liter and a saturated solution, and the chemical reagent in the second compartment comprising alkali-hydroxide in alcohol having a strength of between 0.0001 moles per liter and a saturated solution.

3. The method according to claim 1 which includes mixing said chemical reagents with a third chemical reagent contained within a further compartment within said tube, the chemical reagent in said first compartment comprising alkalihydroxide in water having a strength of between 0.0001 moles per liter and a saturated solution, the chemical reagent in one of said other compartments comprising phosphomolybdic acid in water having a strength of between 0.0001 moles per liter and a saturated solution, the chemical reagent in the other of said compartments comprising glacial acetic acid.

4. An apparatus for measuring the amount of mercaptan-based odorant in natural, synthetic, and L.P. gas in conjunction with flow control means connected to a source of said gas under pressure; comprising in combination a reagent tube, having a closed end and an open end, a first frangible membrane covering said open end and a second frangible membrane spanning said tube intermediate the ends thereof thereby dividing said tube into a pair of compartments sealed from one another, a liquid chemical reagent in each of said compartments and means to introduce said gas into one of said compartments via said first membrane whereby said gas bubbles through said chemical reagent in said one compartment, and means to exhaust said gas through said first membrane.

5. The apparatus according to claim 4 in which said means to introduce said gas into one of said compartments and to exhaust said gas from said compartment, includes a double orifice needle connected to said source of gas, said needle having an inner hollow portion, and an outer hollow exhaust portion concentrically situated around said inner portion, said portions having membrane piercing distal ends, the membrane piercing distal end of said outer portion terminating spaced back from the membrane piercing distal end of said inner portion, said membrane piercing distal end of said outer portion being situated above the liquid reagent level in said one compartment when engaged within said tube, to facilitate the escape of gas bubbling through said reagent.

6. The apparatus according to claim 4 which includes a further membrane spanning said tube intermediate the ends thereof thereby dividing said tube into three compartments, and a liquid chemical reagent in said third compartment.

7. The apparatus according to claim 6 in which said means to introduce said gas into one of said compartments and to exhaust said gas from said compartment, includes a double orifice needle connected to said source of gas, said needle having an inner hollow portion, and an outer hollow exhaust portion concentrically situated around said inner portion, said portions having membrane piercing distal ends, the membrane piercing distal end of said outer portion terminating spaced back from the membrane piercing distal end of said inner portion, said membrane piercing distal end of said outer portion being situated above the liquid reagent level in said one compartment when engaged within said tube, to facilitate the escape of gas bubbling through said reagent.

* * * * *